United States Patent [19]

DeLacy

[11] Patent Number: 4,806,292

[45] Date of Patent: Feb. 21, 1989

[54] SYSTEM FOR STABILIZING DIMENSIONAL PROPERTIES OF CURED COMPOSITE STRUCTURES

[75] Inventor: Thomas J. DeLacy, Los Altos, Calif.

[73] Assignee: Ford Aerospace & Communications Corporation, Detroit, Mich.

[21] Appl. No.: 821,370

[22] Filed: Jan. 21, 1986

[51] Int. Cl.$^4$ .................. G01N 29/04; B29C 65/66; B29C 67/14

[52] U.S. Cl. .................. 264/40.1; 73/587; 264/40.6; 264/236; 264/237; 264/348; 264/347; 425/143

[58] Field of Search .................. 264/40.1, 40.6, 236, 264/347, 348, 237; 425/143; 73/587

[56] References Cited

U.S. PATENT DOCUMENTS

| | | | |
|---|---|---|---|
| 3,713,127 | 1/1973 | Keledy et al. | 340/261 |
| 3,924,456 | 12/1975 | Vahaviolos | 73/88 R |
| 3,934,451 | 1/1976 | Bristoll et al. | 73/15 ED |
| 4,089,224 | 5/1978 | Scott et al. | 73/587 |
| 4,126,033 | 11/1978 | Bartoli et al. | 73/15 A |
| 4,191,718 | 3/1980 | Mallick et al. | 264/236 X |
| 4,255,971 | 3/1981 | Rosencwaig | 73/606 |
| 4,344,142 | 8/1982 | Diehr, II et al. | 264/40.1 X |
| 4,353,255 | 10/1982 | Fukuda et al. | 73/587 |
| 4,380,172 | 4/1983 | Iman et al. | 73/659 |
| 4,430,897 | 2/1984 | Quate | 73/606 |
| 4,455,268 | 6/1984 | Hinrichs et al. | 264/40.6 X |
| 4,484,820 | 11/1984 | Rosencwaig | 374/6 |
| 4,494,408 | 1/1985 | DeLacy | 73/587 |
| 4,515,545 | 5/1985 | Hinrichs et al. | 425/143 |

FOREIGN PATENT DOCUMENTS 1124676  3/1962  Fed. Rep. of Germany ...... 425/143

OTHER PUBLICATIONS

*McGraw-Hill Dictionary of Physics and Mathematics,* Daniel N. Lapedes, Editor in Chief, New York, McGraw-Hill Book Company, 1978.

*Primary Examiner*—Philip Anderson
*Attorney, Agent, or Firm*—Edward J. Radlo; Kenneth R. Allen; Keith L. Zerschling

[57] ABSTRACT

Method and apparatus are disclosed for inducing dimensional stability in cured composite structures using acoustic emission analysis to identify the appropriate level and extent of coincident thermal conditioning. Temperature of the composite structure is lowered at a bounded rate to a minimum temperature typical of the intended operating environment. Passive stress wave acoustic emissions of the composite are analyzed to generate a signature of stress relaxation events over time. When the rate of stress relaxation events decreases below a predetermined percentage of the maximum rate, and remains below that level for a period of time sufficient to predict operational stability, thermal conditioning is terminated.

15 Claims, 3 Drawing Sheets

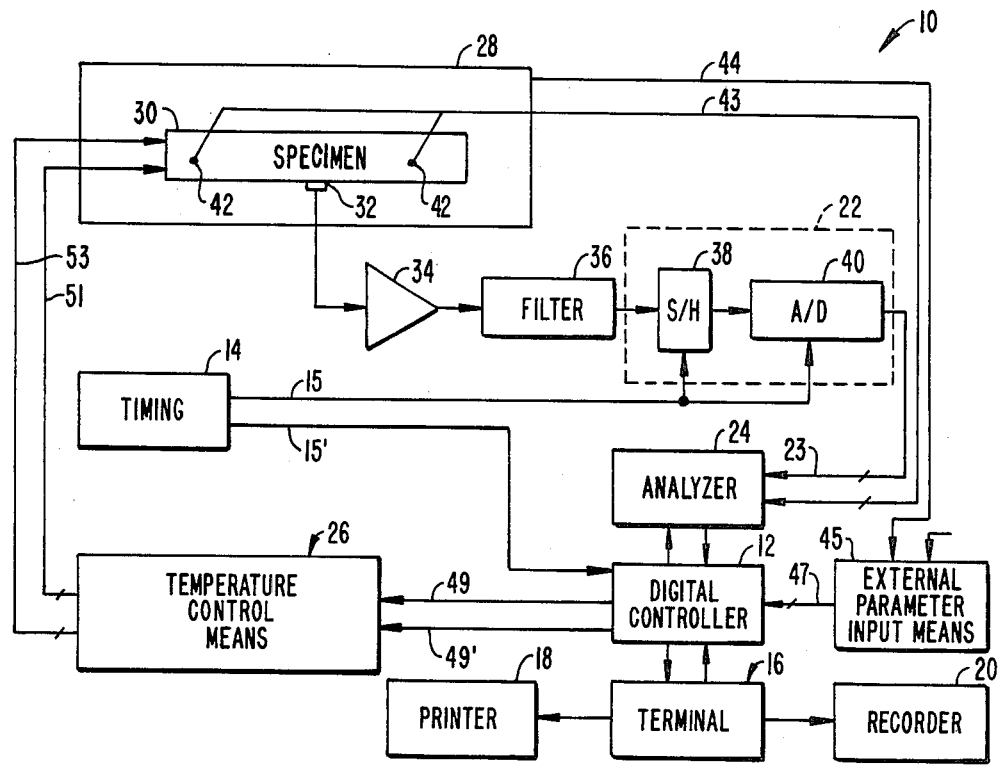
FIG._1.
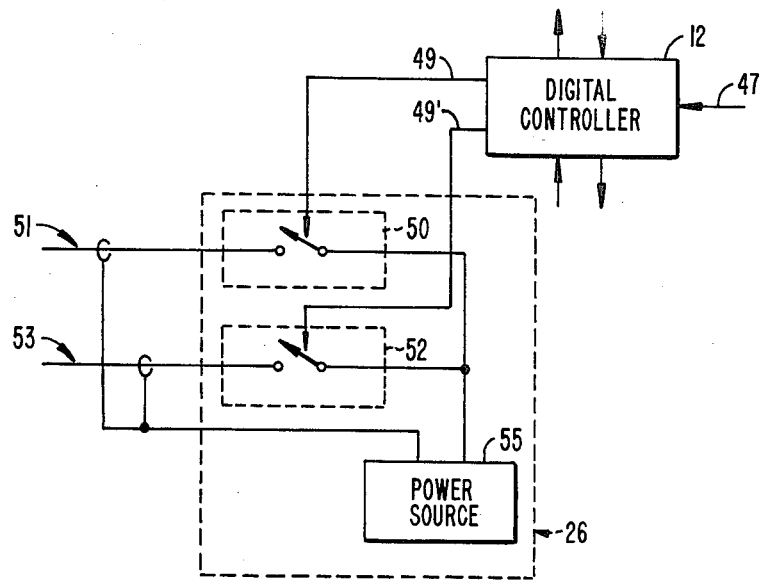
FIG._1A.

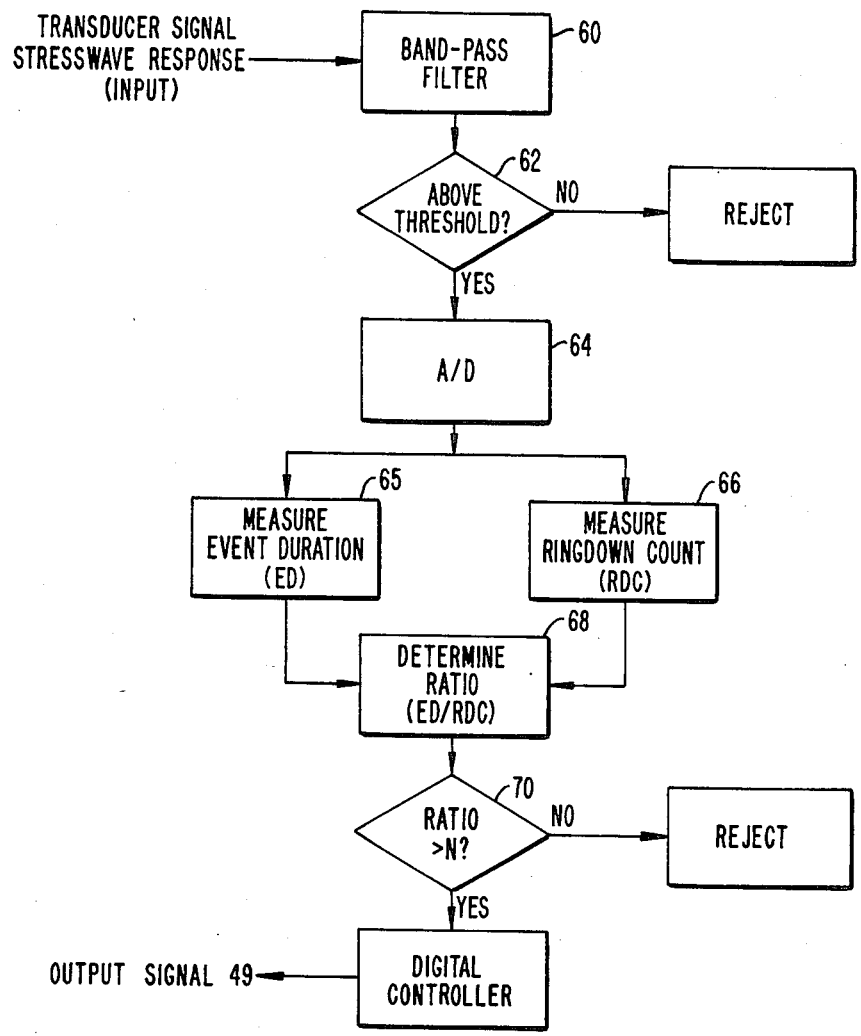
FIG._2.

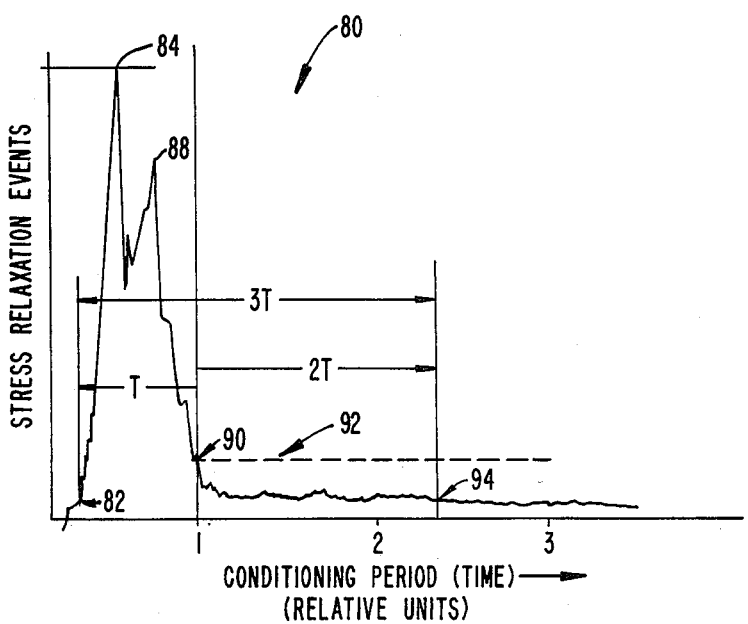
FIG._3.
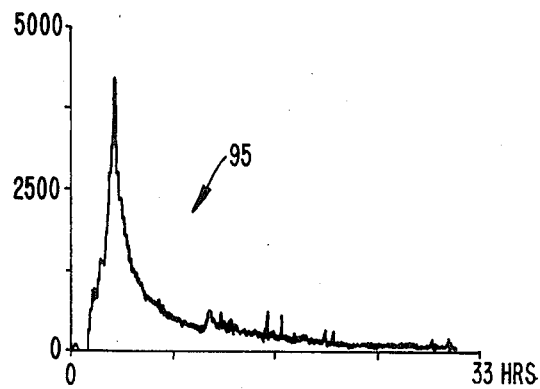
FIG._4.
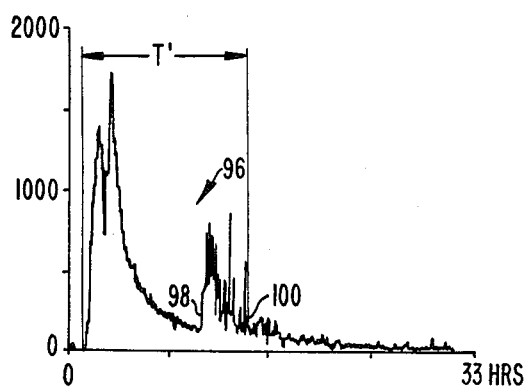
FIG._5.

SYSTEM FOR STABILIZING DIMENSIONAL PROPERTIES OF CURED COMPOSITE STRUCTURES

BACKGROUND OF THE INVENTION

1. Field of Invention

This invention relates to stabilizing the properties of advanced composite materials such as epoxy resin organic carbon fiber composites. In particular, the invention relates to a method and apparatus for inducing potential dimensional stability in cured composite structures by using passive stress wave acoustic emission analysis to determine the appropriate level and extent of coincident thermal conditioning.

Advanced composite materials, primarily graphite and aramid fiber reinforced epoxy resin materials, are attractive to a number of applications due to their high specific stiffness, high strength, and low coefficients of thermal expansion (CTE). Among the applications are antennas and microwave components for satellites and other spacecraft. These applications impose stringent demands on dimensional stability over a broad range of operating temperatures and stress conditions. However, such composite materials are heterogeneous as well as anisotropic. Consequently, thermal treatment, including thermal loading during and subsequent to the formation of the solid state of the material, induces internal residual stresses. These residual stresses are subject to relaxation with time, which results in dimensional modification, the extent of which may be unacceptable in certain critical applications, such as spacecraft antenna systems. Therefore, great interest exists in techniques for inducing controlled stress relaxation in composite structures and for verifying consequent dimensional stability.

2. Description of the Prior Art

The following patents were uncovered in a search of the public records of the U.S. Patent and Trademark Office respecting the subject invention:

| INVENTOR | U.S. PAT. NO. |
| --- | --- |
| Bristoll et al. | 3,934,451 |
| Keledy et al. | 3,713,127 |
| Vahaviolos | 3,924,456 |
| Scott et al. | 4,089,224 |
| Bartoli et al. | 4,126,033 |
| Rosencwaig | 4,255,971 |
| Fukuda et al. | 4,353,255 |
| Imam et al | 4,380,172 |
| Quate | 4,430,897 |
| Rosencwaig | 4,484,820 |

Keledy et al, Vahaviolos, Scott et al, and Fukuda et al disclose acoustic emission monitoring systems which are principally used to monitor crack formation and growth in a structure. There is no disclosure in these patents of conditioning the structure to relieve residual stress.

Bristoll et al. discloses a method of detecting imperfections in a lining of foamed material by first cooling the surface of the lining and then observing the lining for imperfections in the cooled state. There is no disclosure of acoustic emission monitoring or of inducing stress relief to stabilize dimensional properties.

Imam et al. discloses methods for detecting incipient cracks in a turbine rotor in which a signature analysis is used for comparison of vibration patterns after perturbation to normal vibration patterns. There is no suggestion of any mechanism for controlling stress-related characteristics.

Bartoli discloses a method for determining the thermal conductances of binding layers of detectors in infrared detector arrays.

Rosencwaig '820, Quate and Rosencwaig, '971 relate to acoustic and thermoacoustic microscopy.

Additionally, U.S. Pat. No. 4,494,408 was issued Jan. 22, 1985 to the inventor of the present invention and assigned to the same assignee. That patent discloses method and apparatus for monitoring and controlling potential residual stress relief mechanisms in composite materials by acoustic emission signature analysis during the cure cycle. The invention decribed in the present application is distinguished in that it provides extended teachings concerning the use of post-cure constant temperature conditioning to stabilize dimensional properties of composite materials.

SUMMARY OF THE INVENTION

According to the invention, a method and apparatus are provided for stabilizing dimensional properties of advanced composite materials, and particularly for predicting dimensional stability of cured composite structures using acoustic emission analysis while actively stabilizing dimensional properties by controlled thermal conditioning. The invention is based on a discovery that thermal conditioning at a constant temperature may bias the mechanisms of stress relief to induce dimensional stability in composite structures. Furthermore, by analyzing selected interdependent parameters manifest as features of a time-dependent function (herein interdependent waveform features) of the acoustic emissions, it is possible to detect the presence of specific stress relaxation mechanisms in the composite and to thereby generate a signature of stress relaxation events with respect to time. (Events correspond to acoustic reports associated with mechanical stress waves generated upon the breaking of bonds in the subject material. Events are generally identified by the detection of a transient sound having an amplitude above a predetermined threshold and substantially discriminated from sources of external and known noise.) This signature may then be compared against selected criteria to identify a state of stress/strain equilibrium, and corresponding dimensional stability, of the composite.

According to a specific embodiment of the invention, sensor means, such as a passive transducer, sensitive to acoustic signals generated by relaxation of stress mechanisms within the subject composite structure, are coupled to the composite and a controlled thermal load is placed on the subject structure, thereby ramping the temperature at a constant rate to a low limit. Analyzer means receive the signals from the sensor means after conditioning (filtering and thresholding) and digitizing of the signal. The analyzer means analyze the interdependent waveform features, such as one or more ratios of parameters, and compare them to empirically derived data to recognize specific stress relaxation events. When the occurrence rate of such events drops below a level characteristic of dimensional stability, and remains below that level for a specific duration, controller means terminate the thermal conditioning period.

One of the purposes of the invention is to provide noninvasive, in situ means for inducing the relaxation of internal residual stresses (herein stress relaxation response) in advanced composite structures.

Another purpose of the invention is to provide noninvasive, in situ means for recognizing acoustic signals indicative of stress relaxation events in advanced composites.

Another purpose of the invention is to provide constant temperature conditioning in lieu of conventional cyclic temperature conditioning to dissipate induced residual stresses naturally, i.e. via redistribution networking, without degrading mechanical or thermal properties.

Another purpose of the invention is to use the distributed properties response (viscoelastic signature response) of the composite to qualify like properties for quality assurance.

Another purpose of the invention is to provide means for confirming dimensional stability of a composite subject to post-cure thermal condition.

These and other purposes of the invention will be apparent by reference to the following detailed description taken in connection with the accompanying drawings.

BRIEF DESCRIPTION OF THE DRAWINGS

FIG. 1 is a block diagram of an apparatus for monitoring and controlling the post-cure thermal conditioning of advanced composite structures.

FIG. 1A is a schematic diagram showing a temperature control means of FIG. 1.

FIG. 2 is a flow diagram of a method for analyzing acoustic emissions from a composite structure to recognize acoustic signals indicative of stress relaxation events.

FIG. 3 is a representative signature of stress relaxation events over time for a composite structure undergoing thermal conditioning.

FIG. 4 is representative of an actual data plot of a stable composite element showing stress relaxation events per unit time.

FIG. 5 is a representation of an actual data plot of a "quasi"-stable composite element showing stress relaxation events per unit time.

DESCRIPTION OF PREFERRED EMBODIMENT

FIG. 1 illustrates a specific embodiment of a system 10 for stabilizing the dimensional properties of cured composite structures. The structures, as, for example, a specimen 30, are typically formed of graphite fiber reinforced epoxy resin materials, hereinafter referred to as composites, which may be in the form of a tubular element, laminate sheet or other shaped form. The thermal conditioning system 10 comprises a digital controller 12, timing means 14, terminal means 16, printer means 18, recorder means 20, analog-to-digital signal converter means 22, analyzer means 24, temperature control means 26, and a conditioning chamber 28. Specimen 30 of the composite is placed in the conditioning chamber 28 and sensor means 32 are coupled to the specimen 30. Noninvasive coupling of sensor means 32 may be accomplished using a medium having a high viscosity index, such as anti-seizing compound, which will retain its consistency during the temperature excursion applied to the specimen 30. Low thermal expansion tape, such as Kapton tape, may be used to attach the sensor means 32 to the specimen 30. The sensor means 32 should be thermally conditioned prior to attachment to the specimen 30.

The sensor means 32 may comprise a piezo-electric transducer either having a flat (broadband) response or having a suitable resonant response, that is, responsive to acoustic stress waves generated within the specimen between approximately 150 kHz and 2 MHz frequency. The electrical output of the sensor means 32 is coupled to an amplifier 34, the output of which is coupled to a band-pass filter 36. The output of the filter 36 is coupled into signal converter means 22. Signal converter means 22 receives analog input signals at a sample-and-hold circuit 38, the output of which is coupled into an analog-to-digital converter 40. The sample-and-hold circuit 38 and the analog-to-digital converter 40 are clocked by timing means 14 via clock, line 15. The outputs of the signal converter means 2 are coupled into analyzer means 24 via lines 23. Analyzer means 24 may be a programmable 8 bit microprocessor with memory means, or may be other suitable meansffor analyzing the incoming digital signal. Optional thermocouples 42 may be thermally attached to the specimen 30 and coupled via signal lines 43 into analyzer means 24 so that the analyzer means 24 may optionally receive both acoustic and thermal input signals directly from the specimen 30. Additionally, the analyzer means 24 may receive command input and timing input signals from, for example, the digital controller 12.

In general, temperature of the specimen 30 need not be closely correlated with the acoustic signals of specimen 30 when it is subjected to constant temperature loading, as described below for this embodiment. For simplicity, temperature of the ambient environment rather than actual surface temperature of the specimen may be monitored, if constant temperature loading is employed. There are various means for conveying ambient temperature information from the conditioning chamber 28. In the example shown in FIG. 1, ambient temperature signals are conveyed by a line 44 to external parameter input means 45, digitized and conveyed to digital controller 12 via digital input signal bus 47 as a part of the so-called external parameter inputs.

Accepted acoustic signals from analyzer means 24 are coupled into the digital controller 12. The digital controller 12 also receives inputs from timing means 14 via line 15' and from external parameter input means 45 via bus 47, which provides such external parameters as the ambient temperature inside the conditioning chamber, as discussed above.

Referring to FIG. 1A, the digital controller 12 cooperates with the temperature control means 26 via lines 49 and 49'. The digital controller 12 may convey simple on-off signals to temperature control means 26 to alternately regulate heat input and withdrawal from the conditioning chamber 28. The temperature control means 26 may take the form of a first relay 50 and a second relay 52 for switching a power source 55 to a heater (not shown) in the conditioning chamber 28 via line 51 or to a cooler (not shown) in the conditioning chamber 28 via line 53. Line 49 may control relay 50 and line 49' may control relay 52.

Returning to FIG. 1, the digital controller 12 may be bidirectionally coupled to both analyzer means 24 and terminal means 16. The terminal means 16 is for operator interface and for communication to the printing means 18 and recording means 20. In one embodiment the digital controller 12 may therefore be a simple data acquisition and signal processing device to provide controlled temperature regulation, analogous to a thermostat. Alternatively, the digital controller 12 and temperature control means 26 may be in combination a commercially available controller such as the Sym-Com No. 3 temperature controller and Sym-Com 5 digital rate programmer by Sym-Tek company of Santa Clara, Calif. One of the features of these commercial apparatuses is the ability to positively control temperature ramp rate during the initial application of a thermal load.

The invention operates as follows: following attachment of the sensor means 32 to the cured composite specimen 30, the temperature inside the conditioning chamber 28 is first raised, under control of temperature control 26 via line 51, to a level sufficient to drive off volatiles such as moisture which may be absorbed or otherwise entrapped by the specimen 30. The temperature in the conditioning chamber 28 is then lowered under control of temperature control 26 via line 53 ramping the temperature at a constant rate to a low limit. Analyzer means 24 received the signals from the sensor means 32 after conditioning (filtering and thresholding (34, 26)) and digitizing (36, 40) of the signal. The analyzer means 24 analyze the interdependent waveform features such as one or more ratios of parameters, and compare them to empirically-derived data to recognize specific stress relaxation events. When the occurrence rate of such events drops below a level charcteristic of dimensional stability and remains below the level for a specific duration, controller means 12 terminate the thermal conditioning.

The controlled thermal load may be a constant temperature imposed on the composite structure.

The load representative of the operating environment may include increasing the temperature of the composite structure from ambient temperature to an upper limit to drive off volatiles and then decreasing the temperature of the composite at a bounded rate from the upper limit to a low limit to approximately equal to the minimum temperature of the operating environment followed by maintaining the temperature of the composite at the lower limit. The bounded rate may be a rate of less than $-10°$ C./minute.

The lower limit of the imposed temperature conditioning is reaced at approximately $-50°$ C. This load temperature is maintained for the remainder of the conditioning. chamber 28 is then lowered using suitable cooling means, such as, for example a dry nitrogen gas injection system (not shown) under control of temperature control 26 via line 53, The temperature normal rately is lowered according to a bounded ramp rate under control of digital controller 12. The ramp rate should be sufficiently slow to inhibit stress damage which might otherwise, result if a temperature ramp rate is applied which, is extreme in comparison to the maximum is contemplated temperature ramp rate for the contemplated operating environment. The temperature dropped to a level approximating the low temperature limit to which the specimen, will be exposed in actual application and held at that, level. For most applications of thermal conditioning of composite structures for use in spacecraft, the temperature ramp rate generally should not exceed about, $-10°$ C./minute, and is preferably between approximately $-1°$ C./minute and $-5°$ C./minute; the low temperature limit will generally be in the range $-40°$ C. to $-100°$ C., with a typical extreme temperature for a component which is protected in its contemplated operating environment at about $-50°$ C.

The acoustic signals from the sensor means 32 are amplified by the amplifier 34 and conditioned by band-pass filter 36 to remove spurious signals, such as, for example, signals from mechanical noise having a frequency below about 100 kHz. The resulting signals are digitized by signal converter means 22 and sent on to the analyzer 24 for analysis. Acoustic signals desi vered to be monitored from the specimen 30, called accountable signals, i.e., those signals representat of stress relief mechanisms occurring in the specimen 30 in response to the controlled thermal load, are recognized by the analyzer 24 and sent to the controller 12. A signature of the rate of stress relaxation events per unit time versus elapsed conditioning time is extracted from the accountable.

A signature of stress relaxation events with respect to time is extracted from the signals, where stress relaxation events are defined as acoustic reports of the breaking of atomic and/or molecular bonds. The signature of the structure comprises at least indicia at selected times of the rate stress relaxation events per unit time. The extracted signature is compared with selected criteria from a predefined signature template (and optionally preprogrammed limits) to determine whether the indicia satisfy the selected criteria and thus the course and need for continued conditioning. The predefined signature template is derived from an observed response of an equivalent composite structure when exposed to an analogous thermal load. Analyzer means 24 and controller means 12 act together to continuously analyze the signals from sensor 32 to determine the point in time where stress/strain equilibrium is reached. Thereafter the thermal load may, be removed.

In general, temperature control means 26 is controlled by the digital controller 12 for applying heating and cooling for sustained conditioning of the specimen 30, or for terminating the conditioning period in response to the analyzed acoustic signal. Terminal 16 provides means for memory access and programming of analyzer 24 to facilitate on-line diagnostics to study various composite forms, and to initiate changes, such as sampling interval, signal conditioning, and display options. An operator may manually override the controller means 12 to alter the conditioning parameters (via temperature control means 26) according to the analyzed response of the sensor means 32, as observed through printer means 18 and recorder means 20. Timing means 14 provide a clock for initiation and coordination of the interdependent functions for data sampling, analysis, and routing of signals.

The recognition of accountable acoustic signals from the sensor 32 will be understood with reference to FIG. 2. The signal from the sensor 32 is conditioned (60) by the band-pass filter 36, and those components which do not reach a preselected minimum voltage threshold are rejected (62). Specific interdependent parameters, such as event duration, ringdown count, and/or peak amplitude are then measured (65,66). Two or more of these interdependent parameters are then interrelated (68) and compared (70) to empirically derived data correlating to accountable stress relaxation mechanisms. In the preferred embodiment, the interdependent waveform features derived from the parameters are frequency dependent and consist of a quotient derivation equal to the number of threshold crossings (ringdown count) of the signal, divided by event duration (68). Event duration is determined by the elapsed period from the time of the first signal threshold crossing to the last signal threshold crossing, corresponding to the energy of the mechanical wave exciting the attached piezo-electric transducer and its dependent signal decay. Other interdependent waveform features, such as the peak amplitude of the signal divided by the ringdown count, or the energy of the signal divided by the ringdown count, may be substituted within the scope of the invention.

The interdependent waveform features may be used to identify specific stress relaxation mechanisms while discounting the signal from fiber fretting and extraneous electrical and mechanical noise sources. The resulting signature data may be used in conjunction with selected benchmarks from exemplary signature templates to monitor and control thermal conditioning.

A further aspect of the invention is based on the generation and identification of a state of induced stress/strain equilibrium, and corresponding dimensional stability, within the intended operational temperature limits of any given composite form.

Referring to FIG. 3, a representative signature 80 is shown, plotting stress relaxation events per unit time vs. elapsed conditioning time. The point of onset 82 of accountable stress relief is seen where the slope of the curve abruptly rises towards a peak value which is reached at point 84. The onset stress temperature is dependent upon the constituents of the composite and its previous thermal history. In general, the onset stress temperature may be presumed to be based on the previous low-temperature history of the specimen. In the example shown in FIG. 3, the onset stress temperature for significant stress relaxation, corresponding to point 82, is reached at approximately −5° C. during the downward temperature ramping. The measured stress relaxation response is maximum at a point 84 at a time after the lower limit of the imposed temperature conditioning is reached, at approximately −50° C. In this example, this low temperature is maintained for the remainder of the conditioning period.

In the typical case illustrated by FIG. 3, localized stresses continue to develop in the composite (due to redistribution phenomena) for some time after the point of maximum stress 84. It is believed that the viscoelastic response of the composite is responsible for renewed stress relaxation activity, as evidenced by the second peak 88 in the signature. A state of "quasi-stability" is reached at point 90, wherein the rate of stress relaxation events has fallen below a benchmark of approximately ten percent of the maximum sustained acoustic emission event rate response indicated by point 84. The material is considered suitable for its contemplated use when operational stability is reached. Operational stability is defined in terms of a multiple of the elapsed time required to generate a quasi-stable state, as defined above. In the example illustrated by FIG. 3, thermal conditioning continues for an additional time period of at least two times (2T) the duration of the dwell period (T) required to achieve quasi-stability. The dwell period T commences at the onset (point 82) of accountable stress relief. In the example shown, the rate of acoustic emission events continues to remain below the ten percent threshold 92, reaching a point of operational stability as defined above after a period 3T at point 94. If the event rate increases above the ten percent threshold 92, prior to the time represented by point 94, conditioning continues for at least an additional time period equal to two times the duration from the point of onset 82 of accountable stress relief to the last point of quasi-stability (For example, after point 100 of FIG. 5).

FIG. 4 is an example of an actual data plot 95 of a stable composite structure. Once a condition of quasi-stability is reached, it is maintained until operational stability is reached. FIG. 5 is an example of an actual data plot 96 of a sample which would require further conditioning after first reaching quasi-stability as described above. At point 98, the event rate rises before operational stability is reached, thus requiring further conditioning. Conditioning should continue after point 100 for a period of at least twice the dwell period (T') needed to reach quasi-stability at point 100. In general, the period required for conditioning varies with each sample specimen and may range from two to more than thirty hours, depending on the nature of and configuration of the specimen.

By imposing a controlled thermal load on the specimen, while detecting the initiation and arrestment of microcracks or other stress relief mechanisms, it is possible to bias the nature of stress relaxation and to induce and identify a state of operational stability. For example, in the case of graphite-epoxy composites such as represented by the signature of FIG. 3, the incremental strain energy developed as a crack is being formed becomes greater than the stored energy beyond a few fiber diameters of the crack sites, and is independent of any existing crack site. Accordingly if the induced stress is sufficiently high, it is more probable that new cracks will form than that old cracks will propagate in order to stabilize the composite. The viscoelastic behavior exhibited by the composite at low temperatures is utilized to redistribute the induced thermal stresses around neighboring good bonds in a manner which minimizes the residual stresses and the possibility of further change in the material.

The invention has now been explained with reference to a specific embodiment. Other embodiments and applications of the invention will be apparent to those of ordinary skill in the art upon reference to this application. It is therefore not intended that this invention be limited except as indicated by the appended claims.

I claim:

1. A method for post cure treatment of a previously cured heterogeneous anisotropic resin-based organic fiber composite structure for improving dimensional stability in said cured composite structure, said cured composite structure to be used in an operating environment charcterized by thermal stress, said method comprising the steps of:

imposing on said composite structure a controllable thermal load representative of said operating environment;

monitoring acoustic signals from said structure while imposing said controllable thermal load;

extracting from said acoustic signals a signature for said structure, said signature comprising a rate of stress relaxation events per unit time overtime;

comparing said signature with a signature template while imposing said controllable thermal load, said signature template being a record of at least selected benchmarks of rates of stress relaxation events, said signature template being derived from an observed response of an equivalent dimensionally stabilized structure exposed to said thermal load; and removing said thermal load from said composite structure when the differences between said extracted signature and said selected benchmarks of said signature template are minimized, thereby assuring the relaxation of internal residual stresses in said composite structure prior to its use in said operating environment.

2. The method of claim 1 wherein said imposing step comprises exposing said composite structure to a constant temperature 3. The method of claim 1 wherein said imposing step comprises:
increasing the temperature of said composite structure from ambient temperature to an upper limit to drive off volatiles;
decreasing the temperature of said composite at a bounded rate from said upper limit to a lower limit approximately equal to the minimum temperature of said operating environment; and
maintaining the temperature of said composite at said lower limit.

4. The method of claim 3 wherein said decreasing step comprises decreasing said temperature at a rate less than −10° C./minute.

5. The method of claim 1 wherein said extracting step comprises the steps of:
conditioning said acoustic signals to remove unwanted frequency components;
measuring at least a first interdependent parameter and a second interdependent parameter, said first and second parameters being characteristic of said conditioned acoustic signals; and
detecting stress relaxation events by comparing an interrelationship of said first and second interdependent parameters to a predetermined value characteristic of stress relaxation mechanisms in said composite structure.

6. The method of claim 5 wherein said detecting step comprises:
comparing the quotient of said first and second interdependent parameters to a predetermined value indicative of stress relaxation events in said composite structure.

7. The method of claim 1 wherein said extracted signature has for each time value a maximum rate of stress relaxation events and a current rate of stress relaxation events and wherein said benchmarks comprise a decrease of said current rate of stress relaxation events to below a reference level, said reference level being a predetermined percentage of said maximum rate of stress relaxation events.

8. The method of claim 7 wherein said predetermined percentage is approximately ten percent.

9. The method of claim 7 wherein said benchmarks further comprise a time duration for which said rate of stress relaxation events must remain below said reference level before performing said removing step.

10. The method of claim 9 wherein said extracted signature has a time of onset of stress relaxation events and said time duration is a multiple of a dwell period, said dwell period being measured from the time of onset of stress relaxation events to the time at which said rate of stress relaxation events decreases to below said reference level.

11. The method of claim 10 wherein said multiple is approximately two.

12. An apparatus for post cure treatment of a previously cured heterogeneous anisotropic resin-based organic fiber composite structure for improving dimensional stability in said cured composite structure, said cured composite structure to be used in an operating environment characterized by thermal stress, said apparatus comprising;
means for imposing on said composite structure a controllable thermal load representative of said operating environment;
sensor means coupled to said composite structure for monitoring acoustic signals from said structure while imposing said thermal load;
analyzer means coupled to said sensor means for extracting from said acoustic signals a signature for said structure, said signature comprising a rate of stress relaxation events per unit time overtime;
means coupled to said analyzer means for comparing said signature with a signature template while imposing said controllable thermal load, said signature template being a record of at least selected benchmarks of rates of stress relaxation events, said signature template being derived from an observed response of an equivalent structure exposed to said thermal load; and
means coupled to said comparing means for removing said thermal load from said composite structure in response to a signal from said comparing means, said comparing means being operative to transmit a signal to said rmoving means when the differences between said extracted signature and said selected benchmarks are minimized,
thereby assuring the relaxation of internal residual stresses in said composite structure.

13. The apparatus of claim 12 wherein said extracted signature has for each time value a current rate of stress relaxation events, a maximum rate of stress relaxation events, and a time of onset of stress relaxation events, and said comparing means are operative to transmit said signal to said removing means when said current rate of stress relaxation events decrease to below a reference level, and remains below said reference level for a time duration equal to a multiple of a dwell period, said dwell period being mcasured from said time of onset of stress relaxation events to the time at which said current rate of stress relaxation events decreases to below a reference level, said reference level being a predetermined percentage of said maximum rate of stress relaxation events.

14. The apparatus of claim 1 wherein said imposing means comprises
means for increasing the temperature of said composite structure to an upper limit;
means for decreasing the temperature of said composite structure at a constant rate from said upper limit to a lower limit approximately equal to the minimum temperature of said operating environment; and
means for maintaining the temperature of said composite at said lower limit.

15. The apparatus of claim 12 wherein said analyzer means comprise
means for conditioning said acoustic signals to remove unwanted frequency components;
means for measuring at least a first interdependent parameter and a second interdependent parameter characteristic of said conditioned acoustic signals; and
means for detecting stress relaxation events by comparing an interrelationship of said first and second interdependent parameters to a predetermined value characteristic of stress relaxation mechanisms in said structure.

* * * * *